June 8, 1965 F. W. ANDERSON Plant Pat. 2,532
NECTARINE TREE
Filed March 25, 1964
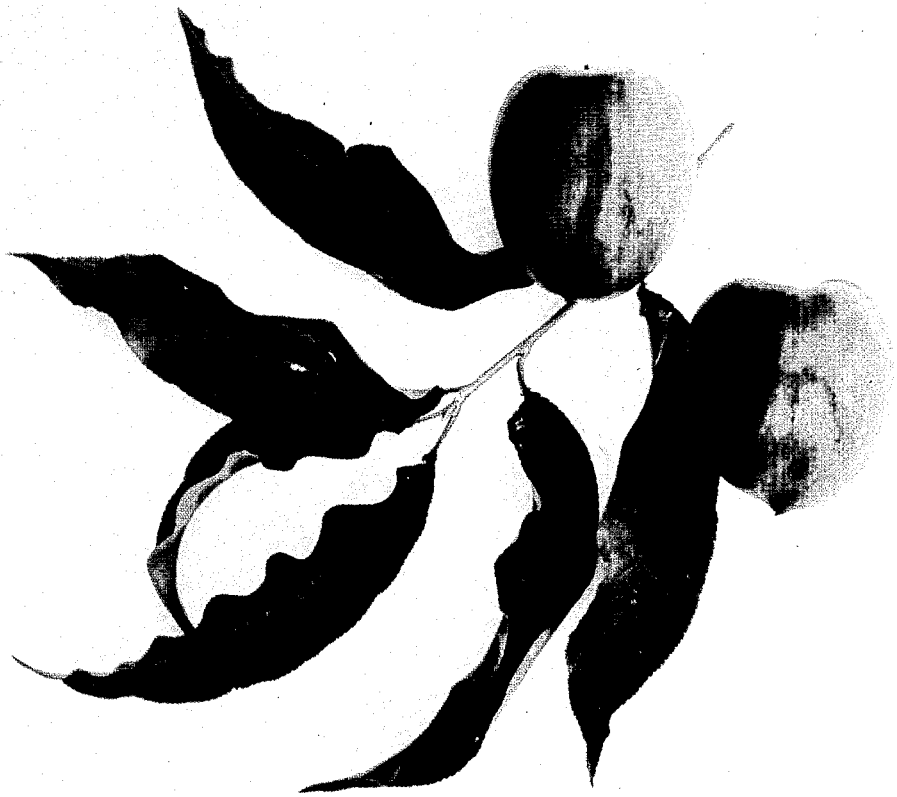
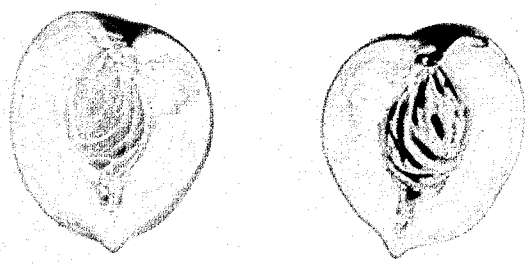
INVENTOR
Frederic W. Anderson
Webster & Webster
ATTYS.

United States Patent Office

Plant Pat. 2,532
Patented June 8, 1965

2,532
NECTARINE TREE

Frederic W. Anderson, Merced, Calif., assignor to George Abe, Selma, Calif.

Filed Mar. 25, 1964, Ser. No. 354,810
1 Claim. (Cl. Plt.—41)

This invention relates to a new and distinct variety of nectarine tree of the type embraced by group 112 in the classification established by Caillavet and Souty in their Monographie des Principales Variétés de Pêchers, 1950 edition; the variety being characterized by large flowers, leaves with reniform glands, and early ripening freestone fruit having a bright red exterior color and flesh which is yellow without red around the stone.

The present variety of nectarine tree is a regular and very productive bearer of fruit which ripens at least two weeks before the John Rivers (unpatented), about ten days before the Merrill Sunrise (United States Plant Patent No. 1,256) and the Grand River (United States Plant Patent No. 1,248), and two to three days before the Red June (United States Plant Patent No. 2,044).

In further comparison to the Red June, the fruit of the present variety remains in firm marketable condition over a substantially longer period of time. Thus, the fruit is of better shipping quality and has a longer shelf life, both being of commercial advantage.

The herein claimed variety of nectarine tree was originated by me as a first generation cross between the Grandandy (United States Plant Patent No. 1,545) and the Grand Haven (United States Plant Patent No. 1,326); such origination of the variety having been accomplished by me in my experimental orchard located near Le Grand, Merced County, California.

Subsequent to origination of the variety, and recognition by me of its novel and distinctive characteristics, as above, I asexually reproduced it in my experimental orchard, located as aforesaid, by top-working on orchard trees. Such asexual reproductions were found to run true to the parent tree in all respects.

The drawing is an illustration, by photographic reproduction in color, of a twig with leaves and fruit at the time of harvest; one fruit being shown as cut in half to expose the flesh and with the stone remaining in one-half.

Referring now more specifically to the pomological details of this new and distinct variety of nectarine tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Vigorous.
- *Growth.*—Spreading.
- *Density.*—Open.
- *Form.*—Vase shaped.
- *Production.*—Very productive.
- *Bearing.*—Regular bearer.

Trunk:
- *Form.*—Medium.
- *Texture.*—Medium.

Branches:
- *Form.*—Medium.
- *Texture.*—Smooth.
- *Color.*—Brown.
- *Lenticels.*—Number—medium. Size—Medium.

Leaves:
- *Size.*—Medium.
- *Thickness.*—Medium.
- *Margin.*—Crenate.
- *Petiole.*—Medium length.
- *Glands.*—Average number and position—2 or 3 on petiole. Alternate; medium size; reniform.
- *Color.*—Top side—medium green (23–J–9). Under side—lighter green (22–J–6).

Flower buds:
- *Size.*—Medium.
- *Length.*—Medium.
- *Form.*—Conic.

Flowers:
- *Date of first bloom.*—March 5, 1963.
- *Date of full bloom.*—March 15, 1963. Medium, as compared with other varieties.
- *Size.*—Large.

Fruit:
- *Maturity when described.*—Eating ripe—June 15, 1963.
- *Date of first picking.*—June 10, 1963.
- *Date of last picking.*—June 20, 1963.
- *Size.*—Uniform; small. Average diameter axially—2¼″. Average transversely in suture plane—2⅛″.
- *Form.*—Uniform; symmetrical; globose to slightly oblong.
- *Suture.*—Shallow, with slight depression beyond pistil point.
- *Ventral surface.*—Rounded slightly.
- *Cavity.*—Rounded, with suture showing on one side. Average depth—3/16″. Average breadth—9/16″.
- *Base.*—Rounded.
- *Apex.*—Short.

Skin:
- *Thickness.*—Medium.
- *Tenacity.*—Free.
- *Tendency to crack.*—None.
- *Down.*—Wanting.
- *Color.*—Yellow ground color (11–K–6) substantially completely overspread with red (4–L–6 to 6–L–6).

Flesh:
- *Juice.*—Abundant.
- *Texture.*—Firm; melting.
- *Fibers.*—Few.
- *Ripens.*—Evenly.
- *Flavor.*—Subacid; vinous.
- *Aroma.*—Very slight.
- *Eating quality.*—Good.
- *Color.*—Yellow (11–L–4), with surface of pit cavity yellow without red.

Stone:
- *Type.*—Free to semi-free.
- *Fibers.*—Long.
- *Size.*—Medium. Average length—1″. Average breath—⅞″. Average thickness—¾″.
- *Form.*—Globose to oblong.
- *Base.*—Straight.
- *Apex.*—Rounded to acute.
- *Sides.*—Equal.
- *Surface.*—Irregularly furrowed throughout; ridged and pitted throughout.
- *Pits.*—Elongated.
- *Ventral edge.*—Thick, without wing toward base.
- *Dorsal edge.*—Full.
- *Ridges.*—Continuous.
- *Tendency to split.*—Slight.
- *Color.*—Tan (12–K–8).
- *Kernels.*—Bitter.

Use: Market; long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

The following is claimed:

A new and distinct variety of nectarine tree, substantially as illustrated and described, characterized by large flowers, leaves with reniform glands, and early ripening freestone fruit having a bright red exterior color and yellow flesh without red around the stone; and further characterized by the regular and very productive bearing of globose to slightly oblong fruit which ripens at least two weeks before the John Rivers, about ten days before the Merrill Sunrise and the Grand River, and two to three days before the Red June, and additionally characterized by fruit which remains firm longer than said Red June.

No references cited.

ABRAHAM G. STONE, *Primary Examiner.*